United States Patent [19]

Emde et al.

[11] 4,447,368

[45] May 8, 1984

[54] PROCESS FOR THE PREPARATION OF AMINOARYLSULPHONIC ACIDS IN SULFOLENE SOLVENT

[75] Inventors: Herbert Emde, Cologne; Heinz U. Blank; Peter Schnegg, both of Odenthal, all of Fed. Rep. of Germany

[73] Assignee: Siemens-Allis, Inc., Atlanta, Ga.

[21] Appl. No.: 364,083

[22] Filed: Mar. 31, 1982

[30] Foreign Application Priority Data

Apr. 11, 1981 [DE] Fed. Rep. of Germany ....... 3114830

[51] Int. Cl.$^3$ .................. C07C 143/56; C07C 143/64
[52] U.S. Cl. .................................... 260/508; 260/509; 260/510; 260/507 R; 260/396 R; 546/192; 546/203; 546/204; 546/205; 546/206; 546/229; 546/232; 546/235; 546/236; 546/238; 548/529; 548/565; 548/577
[58] Field of Search ............... 260/508, 507, 509, 510, 260/369 R; 546/192, 203, 204, 205, 206, 229, 546, 232, 235, 236, 238; 548/577, 529, 565

[56] References Cited

U.S. PATENT DOCUMENTS 3,957,860  5/1976  Lenoir ................................ 260/508

OTHER PUBLICATIONS

Skrowaczeska, Chem. Astr., 48, 7568i–7569i (1954).
Chemical Abstracts, Jul. 12, 1976, vol. 85, No. 2, p. 95, Columbus, Ohio USA T. Hayashi et al., Abstract No. 7242u–T. Hayashi et al., "Catalytic Actions of Mercury (II) Sulfate and Palladium (II) Sulfate for the Sulfonation of . . . ".

Primary Examiner—Nicky Chan
Attorney, Agent, or Firm—John L. James

[57] ABSTRACT

Aromatic aminosulphonic acids which have a reduced content of discoloring by-products are obtained when aromatic amines are reacted with a sulphonating agent in a reaction medium at least some of which consists of tetramethylene sulphone.

19 Claims, No Drawings

PROCESS FOR THE PREPARATION OF AMINOARYLSULPHONIC ACIDS IN SULFOLENE SOLVENT

BACKGROUND OF THE INVENTION

The present invention relates to a process for the preparation of aminoarylsulphonic acids from an arylamine and a sulphonating agent in the presence of tetramethylene sulfone (sulfolane).

It is already known that aromatic aminosulphonic acids are obtained at high temperatures from an arylamine and sulphuric acid (Helv. Chim. Acta. 15, 1372 (1932)). This so-called baking process, in which the corresponding arylammonium sulphate is formed in a first stage, is afflicted by caking phenomena and local superheating, which lead to charring in some cases, undesirable side reactions and hence to reductions in the quality of the product, in particular the color of the product, and to increased expenses for the working-up and purification. Attempts have therefore been made to carry out this baking process in the presence of a solvent or a diluent, to eliminate the defects described or at least to limit them. Examples of solvents proposed for this purpose are o-dichlorobenzene (Ind. Eng. Chem. 42, 1746 (1950)) and diphenyl sulphone (Trav. Soc. Sci. Lettres Wroclaw Ser. B. 61, 5 (1953), cited in C.A. 48, 7568 i (1954)). However, the use of o-dichlorobenzene incurs long reaction times of about 15 to 20 hours and, associated with it, high energy costs. The use of diphenyl sulphone in the baking process produces high yields in some cases, but in some cases it likewise requires long reaction times and it is characterized above all by an involved separation process for the diphenyl sulphone. Because of the high melting point of diphenyl sulphone, which is over 100° C., this working-up cannot be carried out by a simple filtration, but it is possible only by an extraction with benzene, and it is additionally afflicted by the need to recrystallize diphenyl sulphone before it is re-used. The solvents or diluents mentioned here by way of example have the disadvantage in common that, even in their presence, caking phenomena followed by product discolorations cannot be completely avoided, so that purification operations for the product obtained are as necessary as before.

SUMMARY OF THE INVENTION

A process has now been found for the preparation of aminoarylsulphonic acids having a free or neutralized sulphonic acid group, which process is characterized in that an arylamine of the formula

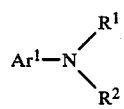
(I)

in which
R$^1$ and R$^2$ independently of one another denote hydrogen, alkyl, aralkyl or aryl, or both together form, together with the N atom on which they are substituted, a nitrogen-containing heterocyclic structure and Ar$^1$ represents an optionally substituted benzene, naphthalene, anthracene, naphthoquinone or anthraquinone skeleton or the skeleton of an aromatic heterocyclic structure, is reacted at a temperatue of 120° to 280° C. with a sulphonating agent in a reaction medium which contains tetramethylene sulphone and, if desired, another inert solvent.

If desired, at least some of the reaction medium, which is recovered, after the reaction is complete, by separation from the aminoarylsulphonic acid formed, which is in a free or salt-type form, is passed back into the reaction without further purification.

DETAILED DESCRIPTION OF THE INVENTION

According to the invention, the reaction medium contains 10 to 2,000 ml, preferably 15 to 1,000 ml, and particularly preferably 20 to 500 ml, of tetramethylene sulphone (sulpholane) per mol of arylamine in the reaction medium.

According to the invention, the reaction medium can contain, in addition to tetramethylene sulphone, other inert solvents, for example in a quantity of 1 to 99% by volume, preferably 10 to 95% by volume, and particularly preferably 50 to 90% by volume, of the total reaction medium, the advantages of working in the presence of tetramethylene sulphone being fully retained. Examples of suitable inert solvents are unsubstituted or alkyl-substituted and/or halogen-substituted aromatics, such as toluene, xylene, ethylbenzene, tetralin, chlorobenzene, dichlorobenzene, trichlorobenzene, tetrachlorobenzene, chlorotoluene, dichlorotoluene, trichlorotoluene, bromobenzene, dibromobenzene, bromotoluene, dibromotoluene, high-boiling aliphatics or mixtures thereof, such as paraffin fractions or kerosene, decalin, isododecane, and also aliphatic sulphones, such as dimethyl sulphone and diethyl sulphone. These solvents can be employed not only singly but also in a mixture, in addition to tetramethylene sulphone, in the reaction medium. The use of inert solvents of this type can have the purpose, for example, of reducing the cost of the entire process by replacing expensive tetramethylene sulphone by less expensive solvents. The addition of such inert solvents can also have the purpose, for example, of optimizing particular separation problems resulting from the large number of substrates to be employed. Such adaptations to the properties of particular substrates are possible in each case by simple preliminary experiments. However, because of the simplicity of handling just one solvent or diluent, it is preferable to employ tetramethylene sulphone as the reaction medium without other inert solvents. Regardless of whether other inert solvents are used or not, sulpholane need not be employed in the process according to the invention in its anhydrous form.

In the process according to the invention, an arylamine is employed which has the general formula

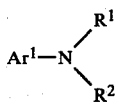
(I)

in which
R$^1$ and R$^2$ independently of one another denote hydrogen, alkyl, aralkyl or aryl, or both together form, together with the N atom on which they are substituted, a nitrogen-containing heterocyclic structure and Ar¹ represents an optionally substituted benzene, naphthalene, anthracene, naphthoquinone or anthraquinone skeleton or the skeleton of an aromatic heterocyclic structure.

Examples which may be mentioned of alkyl are those alkyls which have 1 to 8, preferably 1 to 4, preferably 1 to 2, C atoms, such as methyl, ethyl, propyl, isopropyl, butyl, isobutyl, hexyl or octyl. Examples which may be mentioned of aralkyl are benzyl, 1-phenylethyl, 2-phenylethyl, naphthylmethyl, naphthylethyl, anthrylmethyl and anthrylethyl, preferably benzyl.

Examples which may be mentioned of aryl are phenyl, substituted phenyl, naphthyl and diphenyl, preferably phenyl.

In the event that $R^1$ and $R^2$ together form, together with the N atom on which they are substituted, a nitrogen-containing heterocyclic structure, examples which may be mentioned of the latter are those which have 4 to 8, preferably 5 or 6, ring members, such as pyrroline, pyrrolidine or piperidine.

In the event that $Ar^1$ represents a substituted benzene, naphthalene, anthracene, naphthoquinone or anthraquinone skeleton, for example a number of up to three further substituents, preferably up to two substituents, in addition to an amino group —$NR^1R^2$ may be mentioned, the substituents being so located that at least one ortho- or p-position is unsubstituted. Examples which may be mentioned of substituents are alkyl, within the scope of the abovementioned range of meaning, trifluoromethyl, perfluoroethyl, further phenyl, alkoxy having 1 to 4, preferably 1 to 2, C atoms, such as methoxy, ethoxy, propoxy, isopropoxy, butoxy and isobutoxy, alkylthio, such as thio analogues of the alkoxy groups mentioned, halogen, such as fluorine, chlorine and bromine, and also hydroxyl, nitro, optionally substituted amino, $SO_3H$ and carboxyl. Preferred substituents which may be mentioned are methyl, ethyl, halogenomethyl, phenyl, methoxy, ethoxy, halogen, hydroxyl, nitro, optionally substituted amino, $SO_3H$ and carboxyl and also alkylsulphonyl and arylsulphonyl, such as methylsulphonyl, ethylsulphonyl and phenylsulphonyl. Very particularly preferred substituents which may be mentioned are methyl, chlorine, bromine, fluorine, methoxy and ethoxy.

Preferred arylamines which can be used according to the invention are those of the formula

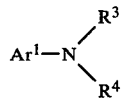  (II)

in which
Ar¹ has the meaning mentioned and
$R^3$ and $R^4$ independently of one another represent hydrogen or alkyl.

Particularly preferred arylamines for the process according to the invention are those of the formula $$Ar^1\text{—}NH_2 \quad (III)$$

in which
Ar¹ has the meaning mentioned.

Further preferred arylamines for the process according to the invention are those of the formula

in which
$R^1$ and $R^2$ have the abovementioned meaning and
$Ar^2$ represents the benzene or naphthalene skeleton.

Further particularly preferred arylamines for the process according to the invention are those of the formula

in which
$R^3$, $R^4$ and $Ar^2$ have the meaning mentioned.
Arylamines of the formula

in which
$Ar^2$ has the meaning mentioned, are very particularly preferably employed.

Examples of arylamines which can be used in the process according to the invention are aniline, o-toluidine, m-toluidine, p-toluidine, 2,4-dimethylaniline, 2,3-dimethylaniline, 2,6-dimethylaniline 2,5-dimethylaniline, N-methylaniline, N-ethylaniline, N,N-dimethylaniline, diphenylamine, p-chloroaniline, 2,4-dichloroaniline, o-chloroaniline, 2,3-dichloroaniline, 3,5-dichloroaniline, 2,5-dichloroaniline, 2,6-dichloroaniline, m-chloroaniline, 2-amino-6-chlorotoluene, 2-amino-5-chlorotoluene, 2-amino-4-chlorotoluene, 2-methoxy-5-methylaniline, p-methoxy-aniline, o-nitroaniline, m-nitroaniline, p-nitroaniline, α-naphthylamine, p-phenylenediamine, m-phenylenediamine, aminodiphenyl, p-nitrodiphenylamine, 2-methoxy-4-nitroaniline, 1-amino-2-ethoxynaphthalene, 1-amino-2-hydroxynaphthalene, 1-amino-8-hydroxynaphthalene, 1-amino-5-hydroxynaphthalene, 1,8-diaminonaphthalene, 1,5-diaminonaphthalene, 2-amino-3-hydroxynaphthalene, 2-aminopyridine, 3-chloro-4-methoxyaniline, 2-aminobenzoic acid, p-ethoxyaniline, 3,4-dichloroaniline, o-fluoroaniline, m-fluoroaniline, p-fluoroaniline, 2-amino-3-chlorotoluene, 3-amino-2-chlorotoluene, 5-amino-2-chlorotoluene, 3-amino-5-chlorotoluene, 3-amino-4-chlorotoluene, 4-amino-3-chlorotoluene, 4-amino-2-chlorotoluene, 5-methoxy-2-methylaniline, 2,3-, 2,4-, 2,5-, 2,6-, 3,4-, 3,5-dimethoxy and diethoxyaniline, o-methoxyaniline, m-methoxyaniline, N-acetyl-p-phenylenediamine, 2-chloro-4-methoxyaniline, 2-chloro-3-methoxyaniline, 4-chloro-3-methoxyaniline, 5-chloro-3-methoxyaniline, 2-chloro-5-methoxyaniline, 3-chloro-2-methoxyaniline, 4-chloro-2-methoxyaniline, 5-chloro-2-methoxyaniline, 2-chloro-6-methoxyaniline and also analogous chloroethoxyanilines, 3-amino-6-chlorobenzoic acid, o-trifluoromethylaniline, m-trifluoromethylaniline, p-trifluoromethylaniline, aminoanthraquinones, such as, for example, 1-aminoanthraquinone or 1,5-diaminoanthraquinone, benzidine and dehydrothiotoluidine.

Examples which may be mentioned of sulphonating agents for the process according to the invention are sulphuric acid, halogenosulphonic acids, such as fluorosulphonic acid and chlorosulphonic acid, sulphur trioxide, amidosulphonic acid, and acid salts of sulphuric acid or a mixture of a sulphate and sulphuric acid.

According to the invention, for example 0.5 to 2.0 mols of sulphonating agent are employed per mol of arylamine, preferably 0.95 to 1.05, particularly preferably 0.98 to 1.02, and very particularly preferably 1 mol of sulphonating agent per mol of arylamine.

The sulphonating agents mentioned can be used on their own. However, it is also possible to use some of the agents mentioned in the form of a mixture; thus, for example, mixtures of various halogenosulphonic acids, of sulphuric acid with one or more halogenosulphonic acids, and of sulphuric acid with sulphur trioxide as oleum having 1 to 65% by weight of $SO_3$. Furthermore, mixtures of sulphuric acid and sulphur trioxide can be used in which the content of sulphuric acid can be 0–35%. However, in many cases it will be advantageous, from the point of view of an easy management of the reaction, to employ only one of the sulphonating agents mentioned. In the event that sulphuric acid is used as a sulphonating agent, it can have a water content of 0 to 50% by weight, preferably 0 to 30% by weight, and particularly preferably 0 to 10% by weight. This dilution water of sulphuric acid can be distilled from the reaction batch together with the reaction water resulting from the substrates, when carrying out the reaction according to the invention. In this process variant, for example one of the abovementioned solvents can serve as an entraining agent in the removal of water from the reaction mixture. However, the distilling-off of dilution water and/or reaction water is in principle also possible without an additional water-entraining agent. In the event that halogenosulphonic acids are employed as a sulphonating agent, the hydrogen halide formed is discharged from the reaction batch to complete the reaction. In the event that $SO_3$ is used as a sulphonating agent, it can be employed in a gaseous or liquid form, it being possible when using the gaseous form to mix the $SO_3$ with an inert gas, such as nitrogen, $CO_2$ or argon, and when using the liquid form to use, in addition, a solvent, for example sulphuric acid in the form of the previously mentioned oleum or also one of the abovementioned solvents. When using sulphur trioxide neither water nor a hydrogen halide need be split off as a condensation product. In addition, a very short reaction time is sufficient here in most cases. In the event that sulphur trioxide is used as a sulphonating agent and the solvent employed contains water, an excess of $SO_3$ can be used or conditions must be selected for a part of the sulphonating reaction as are required when using sulphuric acid as a sulphonating agent.

When using amidosulphonic acid, ammonium salts of the sulphonic acid can be simply isolated instead of the free sulphonic acid. It has been observed that under the conditions according to the invention 2 mols of amidosulphonic acid have to be employed to have 1 mol thereof available as an effective sulphonating agent. The above-mentioned amounts of sulphonating agent per mol of arylamine must therefore be doubled in the case of amidosulphonic acid.

When using an acid salt of sulphuric acid or a sulphate in a mixture with sulphuric acid, aminoarylsulphonic acids can likewise be prepared in an elegant and direct manner. This mixture consists of about equimolar amounts of the sulphate and of sulphuric acid. Examples which may be mentioned here of hydrogen sulphates or sulphates which can be used according to the invention are the soluble salts of alkali metals and of alkaline earth metals, and also of the ammonium ions, such as those of lithium, sodium, potassium, rubidium, caesium, ammonium, magnesium and calcium, preferably the salts of ammonium, sodium or potassium.

The sulphonating agent used is preferably at least one member from the group comprising sulphuric acid, $SO_3$ and chlorosulphonic acid, it being possible, when using sulphuric acid alone, for it to have a water content as disclosed above, preferably of 0 to 30% by weight.

The reactants can be added in various sequences to the reaction vessel. Thus, either the arylamine or the sulphonating agent are initially introduced into tetramethylene sulphone and the respective second component is added in a pure form or diluted with tetramethylene sulphone or with one of the other solvents mentioned. It is likewise possible to meter in simultaneously the two components, on their own or together, in the form of a solution or a melt, the tetramethylene sulphone either being initially introduced into the reactor or added as a diluent or solvent together with the mixture of the reactants or divided into the individual streams of the reactants.

The solution or suspension prepared in one of the ways described from the starting products and tetramethylene sulphone or other solvents is then heated, for example, to 120° to 280° C. or preferably to 150° to 260° C. and particularly preferably to 160° to 240° C., during which period eliminated water or an eliminated hydrogen halide, either of which may be present, is removed from the reaction medium.

In a further variant, tetramethylene sulphone and an optionally co-used further inert solvent can also be heated to a temperature within the range mentioned, and the starting materials can be added in the form of a melt, suspension or solution to the hot reaction medium initially introduced.

The process can be carried out continuously or discontinuously.

The process can be carried out in principle in vacuo, under atmospheric pressure or under an overpressure. In some cases an overpressure can be advantageous, for example to reach a higher reaction temperature in the presence of a low-boiling solvent. For example, a pressure of from 0.1 to 100 bar, especially of from 1 to 20 bar, may be mentioned. However, in some cases it can also be advantageous to apply a vacuum, for example in the case of high-boiling solvents when it is intended to work under reflux conditions or in the case of a sulphonation of heat-sensitive arylamines.

To work up the reaction batch and to separate off the aminoarylsulphonic acid formed, various variants are possible, in which the aminoarylsulphonic acid is isolated in a free or in a salt-type form. Thus, in many cases the precipitated aminoarylsulphonic acid can be separated from the reaction medium by a simple filtration. In the event that tetramethylene sulphone is used as a reaction medium without another inert solvent, a complete precipitation of the aminoarylsulphonic acid formed can also be effected by the addition of water. In this case, for example after the filtering-off, the tetramethylene sulphone is displaced from the filter cake with water. In the event that a salt of the aminoarylsulphonic acid was not already obtained during the reaction, by one of the variants described, this can be effected in the working-up by the addition of aqueous alkali to the reaction batch, which produces a precipitate of the corresponding salt of the aminoarylsulphonic acid. Examples which may be mentioned of an aqueous alkali for this variant are a solution or suspension of ammonia, lithium hydroxide, sodium hydroxide, potassium hydroxide, magnesium oxide or hydroxide, and calcium hydroxide. In a further variant, the precipitation of ammonium salts of aminoarylsulphonic acids can be achieved, even in a water-free working-up, by introducing ammonia or an aliphatic amine into the reaction batch.

Tetramethylene sulphone isolated in one of the working-up variants mentioned, as a filtrate, possibly in a mixture with a further inert solvent, can be passed back into the process according to the invention without further purification. In the event that $SO_3$ or a halogenosulphonic acid or a mixture containing these is used as a sulphonating agent, it is advantageous, however, to distil off any water which may be present in the tetramethylene sulphone to be re-used before the re-use, to prevent substantially the decomposition of the sulphonating agents mentioned. However, in the event that, for example, sulphuric acid or a water-containing sulphuric acid is used as a sulphonating agent, a low water content in the reintroduced tetramethylene sulphone is not troublesome and can be distilled from the next reaction batch together with the reaction water. However, if recovered tetramethylene sulphone has a higher water content, it can be advantageous to distil off this water or at least a part thereof before the re-use. Filtrates obtained on displacing tetramethylene sulphone from a filter cake with the aid of water are advantageously collected separately and are used in the working-up variants described above as far as possible, instead of the addition of pure water to the reaction mixture.

The process according to the invention makes it possible to overcome the disadvantages of variants of the so-called baking process which have become known up to now, the disadvantages being occasionally very long reaction times, caking phenomena on reactor walls, associated impairments of the product and additionally necessary purification stages and, connected with this, yields which are frequently only very small, in particular in the case of heat-sensitive amines, and also the formation of isomers and disulphonation.

Tetramethylene sulphone or solvents or diluents containing tetramethylene sulphone, in contrast to the previously known variants, yield, according to the invention, extremely pure products in very short reaction times. The reaction can be carried out in very high amine/sulphonating agent concentrations, relative to tetramethylene sulphone or its content in the reaction medium, without problems regarding stirring or caking arising. Excellent space-time and material yields are obtained thereby. The resistance of tetramethylene sulphone to acids and bases and its low toxicity are also advantageous as regards the choice of reactor material and as regards health and safety conditions at work (J. Martinmaa, The Chemistry of Non-Aqueous Solvents; Academic Press, New York 1976, Vol. IX, page 247 et seq.). In the event that the reaction is carried out in tetramethylene sulphone as the reaction medium without other inert solvents, the further advantage to be mentioned is that tetramethylene sulphone does not appear in the distillate obtained on distilling off water, a state of affairs arising in the case of solvents used hitherto in accordance with the state of the art. To purify and pass back these co-distilled solvents, a considerable amount of energy had to be expended up to now, which is unnecessary in the process according to the invention.

Generally, tetramethylene sulphone shows the following advantages with respect to the inventive process; it is distillable for purification; it is water-soluble and may be removed easily with water from the reaction product; it is liquid at room temperature and therefore the main amount may be removed by filtration from the reaction product.

Aminoarylsulphonic acids which can be obtained in the process according to the invention are valuable intermediate products in the preparation of pharmaceuticals, foamed plastics, optical brighteners, wetting agents, synthetic mordants, tanning agents, resist agents, insecticides, finishing agents, softeners and polymeric thickeners (Ullmanns Encyclopadie der technischen Chemie [Ullmann's Encyclopaedia of Industrial Chemistry], 3rd edition, volume 16, page 561, Verlag Urban und Schwarzenberg, Munich/Berlin 1965).

EXAMPLE 1

232.8 g (2.50 mols) of aniline are initially introduced into 500 ml of hot sulpholane at 85° C., and 245.3 g (2.50 mols) of 100% strength sulphuric acid are added dropwise without cooling. During this stage the temperature is allowed to rise to 160° C. The readily stirrable anilinium sulphate suspension melts on heating at about 165° C. The reaction water is distilled off in the course of 1.5 hours at an internal temperature of 180°–192° C. p-Sulphanilic acid is obtained as a white product in the form of fine crystals. This is filtered off with suction and dried at 130° C. and under 200 mm Hg. The weight of the precipitate is 431.3 g, and the yield of p-sulphanilic acid is 98.9%, and the content is 99.3% by weight.

EXAMPLE 2

232.8 g (2.50 mols) of aniline are initially introduced into 500 ml of hot sulpholane at 85° C., and 255.5 g (2.50 mols) of 96% strength sulphuric acid are added dropwise without cooling. The sulphonation and the working-up are carried out as described in Example 1. The yield of p-sulphanilic acid is 94.4%.

EXAMPLE 3

232.8 g (2.50 mols) of aniline are initially introduced into 500 ml of hot sulpholane at 85° C., and 350.4 g (2.50 mols) of 70% strength sulphuric acid are added dropwise without cooling. The sulphonation and the working-up are carried out as described in Example 1. The yield of p-sulphanilic acid is 95.9%.

EXAMPLE 4

232.8 g (2.50 mols) of aniline are initially introduced into 500 ml of hot sulpholane at 85° C., and 257.5 g (2.625 mols) of 100% strength $H_2SO_4$ are added dropwise without cooling; the mixture is heated to 178° C., and the reaction water is distilled off, during which period the temperature increases to 195° C. The yield of p-sulphanilic acid is 97.2%, relative to aniline.

EXAMPLE 5

247.7 g (2.525 mols) of aniline are reacted in 500 ml of sulpholane with 245.3 g (2.50 mols) of 100% strength $H_2SO_4$, as described in Example 1. A yield of p-sulphanilic acid of 95.9% is obtained.

EXAMPLE 6

232.8 g (2.50 mols) of aniline are initially introduced into 250 ml of hot sulpholane at 85° C., and 245.3 g (2.50 mols) of 100% strength $H_2SO_4$ are added dropwise without cooling in the course of 18 minutes. The reaction water is distilled off in the course of 45 minutes at a reaction temperature of 195° C. 300 ml of water are added at 100° C. to the viscous suspension, the solids of which are filtered off with suction. The wash water is distilled from the mother liquor, and the resulting p-sulphanilic acid precipitate is also filtered off with suction. The precipitates are dried together. The yield of p-sulphanilic acid is 95.7%.

EXAMPLE 7

93.1 g (1.0 mol) of aniline are initially introduced into 500 ml of sulpholane at room temperature. 80.1 g of gaseous sulphur trioxide are passed in at this temperature in the course of one hour, and, after the addition is complete, the temperature is increased to 180° C. The mixture is stirred for 2 hours at this temperature. The working-up is carried out as described in Example 1. The yield of p-sulphanilic acid is 96.6%.

EXAMPLE 8

93.1 g (1.0 mol) of aniline are initially introduced into 500 ml of sulpholane at room temperature. 80.1 g (1.0 mol) of gaseous sulphur trioxide are passed at this temperature over the solution. The suspension is then stirred for 1 hour at 195° C. and it thickens. 200 ml of water are added, and the precipitate is filtered off with suction. The yield of p-sulphanilic acid is 95.1%.

EXAMPLE 9

93.1 g (1.0 mol) of aniline are initially introduced at 150° C. into 500 ml of sulpholane. 116.5 g (0.98 mol) of chlorosulphonic acid (98% strength) are added dropwise in the course of 18 minutes, a vigorous evolution of HCl commencing towards the end of the reaction. The mixture is further stirred for 6 hours under reflux, the temperature falling from 177° C. to 161° C. p-Sulphanilic acid which precipitates is filtered off with suction, the mother liquor is concentrated by evaporation, and the two precipitates are dried. The yield of p-sulphanilic acid is 97.2%.

EXAMPLE 10

186.2 g (2.0 mols) of aniline are initially introduced into 500 ml of sulpholane at room temperature, and 116.5 g (0.98 mol) of chlorosulphonic acid (98% strength) are added dropwise in the course of 13 minutes, during which period the temperature increases to 100° C. The white, viscous suspension is heated for 2 hours under reflux, during which period the temperature increases from 172° C. to 180° C. The working-up is carried out as described in Example 9. The yield is 95.5%.

EXAMPLE 11

93.1 g (1.0 mol) of aniline are heated together with 195.4 g (2.0 mols) of amidosulphonic acid (99.3% strength) in 500 ml of sulpholane to 173° C. Stirring is continued for a further 2 hours, during which period the temperature drops to 135° C. The precipitate is filtered off with suction at 120° C. and dried. It consists mainly of the ammonium salt of p-sulphanilic acid. The yield, calculated as p-sulphanilic acid, is 92.8%.

EXAMPLE 12

127.6 g (1.0 mol) of o-chloroaniline, dissolved in 500 ml of sulpholane, are initially introduced at room temperature, and 98.1 g (1.0 mol) of 100% strength $H_2SO_4$ are added dropwise without cooling. The pale yellow warm suspension at 76° C. is heated to 180° C., and the reaction water is distilled off at this temperature via a 20 cm column with a silver-coated jacket. The temperature increases to 194° C. in the course of the reaction time of 1.5 hours. 3 ml = 3.6 g (0.03 mol) of o-chloroaniline pass over together with the water and can be recovered by phase separation. The suspension is cooled to 160° C., and its solids are filtered off with suction and dried. The yield of 4-amino-3-chlorobenzenesulphonic acid is 93.8%.

EXAMPLE 13

127.6 g (1.0 mol) of m-chloroaniline are initially introduced into 500 ml of sulpholane, and 98.1 g (1.0 mol) of 100% strength $H_2SO_4$ are added dropwise in the course of 9 minutes. The temperature increases to 81° C., and a solid which has a light beige colour precipitates. The batch is heated to 218° C. and everything is dissolved. The reaction water is distilled off at this temperature in the course of 2.5 hours. The residue is cooled to room temperature and the precipitate is filtered off with suction. The yield of 2-amino-4-chlorobenzenesulphonic acid is 89.7%.

EXAMPLE 14

127.6 g (1.0 mol) of p-chloroaniline are initially introduced at 85° C. into 500 ml of sulpholane, and 98.1 g (1.0 mol) of 100% strength $H_2SO_4$ are added dropwise in the course of 10 minutes, during which period the temperature increases to 123° C. The brown solution is heated to 172° C., and the reaction water is distilled off under a reduced pressure of 130–150 mm Hg and at a temperature of 172°–196° C. The suspension is cooled to 160° C. and its solids are filtered off with suction. The yield of 2-amino-5-chlorobenzenesulphonic acid is 95.7%.

EXAMPLE 15

107.2 g (1.0 mol) of o-toluidine are dissolved in 500 ml of sulpholane, and 98.1 g (1.0 mol) of 100% strength $H_2SO_4$ are added to the solution in the course of 8 minutes. During the dropwise addition the temperature increases to 77° C. At the start of the addition of sulphuric acid a suspension is produced, which has turned into a solution by the end of the addition. The reaction water is distilled off at a reaction temperature of 184°–200° C. in the course of 1.5 hours. The suspension is then cooled to 120° C. and its solids are filtered off with suction. The yield of 4-amino-3-methylbenzenesulphonic acid is 93.8%.

EXAMPLE 16

107.2 g (1.0 mol) of m-toluidine are initially introduced into 500 ml of sulpholane, 98.1 g (1.0 mol) of 100% strength $H_2SO_4$ are added dropwise in the course of 10 minutes, during which period the temperature increases to 81° C., and a pale beige solid precipitates. The solid is dissolved on heating to a reaction temperature of 191° C. The reaction water is distilled off in the course of 2 hours at a temperature of 191°–216° C. The resulting suspension is cooled to 160° C. and its solids are filtered off with suction. The yield of 4-amino-2-methylbenzenesulphonic acid is 86.6%.

EXAMPLE 17

107.2 g (1.0 mol) of p-toluidine are initially introduced into 500 ml of sulpholane, and 98.1 g (1.0 mol) of 100% strength $H_2SO_4$ are added in the course of 10 minutes. The warm suspension, now at 80° C., is heated to 178° C., the suspended solids being dissolved. The reaction water is distilled off at 178°–198° C. in the course of 3 hours. 200 ml of sulpholane are distilled from the suspension, which is then cooled to room temperature, and its solids are filtered off with suction. The yield of 2-amino-5-methylbenzenesulphonic acid is 89.6%.

EXAMPLE 18

141.5 g (1.0 mol) of 4-amino-2-chlorotoluene are initially introduced into 500 ml of sulpholane, and 99.1 g (1.01 mols) of 100% strength $H_2SO_4$ are added dropwise in the course of 15 minutes, during which period the temperature increases to 80° C. The mixture is heated to 207° C., and the reaction water is distilled off in the course of 1.5 hours, during which period the temperature increases to 218° C. The suspension is cooled to room temperature. The yield of 2-amino-4-chloro-5-methylbenzenesulphonic acid is 91.0%.

EXAMPLE 19

141.5 g (0.99 mol) of 99% pure 5-amino-2-chlorotoluene are dissolved in 500 ml of sulpholane, and 99.1 g (1.01 mols) of 100% strength $H_2SO_4$ are added over 10 minutes, during which period the temperature increases to 86° C. The reaction water is distilled off at 207°–220° C. in the course of 1.5 hours. The suspension is cooled to room temperature and its solids are filtered off with suction. The yield of 2-amino-5-chloro-4-methylbenzenesulphonic acid is 85.2%.

EXAMPLE 20

137.1 g (1.0 mol) of 2-methoxy-5-methylaniline, dissolved in 500 ml of sulpholane, are initially introduced at 85° C., and 98.1 g (1.0 mol) of 100% strength $H_2SO_4$ are added. A vacuum of 160–100 mbar is applied, the temperature is raised to 152°–163° C., and the reaction water is distilled off in the course of 1.5 hours. The solids of the suspension are filtered off with suction at 150° C. and dried. The yield of 4-amino-5-methoxy-2-methylbenzenesulphonic acid is 98.5%.

EXAMPLE 21

121.2 g (1.0 mol) of 2,4-dimethylaniline are initially introduced into 500 ml of sulpholane, and 98.1 g (1.0 mol) of 100% strength $H_2SO_4$ are added dropwise without cooling. The temperature is gradually increased to 188° C., during which heating-up period the pressure is reduced from 170 to 118 mbar, and the reaction water is distilled off in the course of 2 hours. The batch is evaporated to dryness. The yield of 2-amino-3,5-dimethylbenzenesulphonic acid is 87.0%.

EXAMPLE 22

94.5 g (0.66 mol) of α-naphthylamine are dissolved in 500 ml of sulpholane, and 64.7 g (0.66 mol) of 100% strength $H_2SO_4$ are added dropwise at a maximum temperature of 90° C. The solution is heated under a pressure of 110 mbar to 180° C., and the reaction water is distilled off in the course of 2 hours. The solids of the suspension are filtered off hot and dried. Yield of 4-amino-naphthalene-1-sulphonic acid is 89%.

EXAMPLE 23

159.2 g (1.0 mol) of 5-amino-1-hydroxynaphthalene are dissolved at 57° C. in 500 ml of sulpholane, and 98.1 g (1.0 mol) of 100% strength $H_2SO_4$ are added in the course of 10 minutes. The temperature increases to 86° C. The reaction water is distilled off at 172°–190° C. in the course of 2.75 hours, and the solids of the resulting suspension are filtered off with suction at 120° C. and dried. The yield of 4-amino-8-hydroxynaphthalene-1-sulphonic acid is 71.2%.

EXAMPLE 24

232.8 g (2.50 mols) of aniline are initially introduced into a mixture of 50 ml of sulpholane and 450 ml of 1,2,4-trichlorobenzene, and 245.3 g (2.50 mols) of 100% strength $H_2SO_4$ are added without cooling. The reaction water is distilled off at a temperature of 174°–186° C. in the course of 4.5 hours via a 13 cm column. The batch is cooled to 120° C., and the solids of the suspension are filtered off with suction. The yield of p-sulphanilic acid is 96.3%.

EXAMPLE 25

235.1 g (2.525 mols) of aniline are dissolved in a mixture of 150 ml of sulpholane and 350 ml of 1,2-dichlorobenzene, and 245 g (2.50 mols) of 100% strength $H_2SO_4$ are added in the course of 16 minutes. The mixture is heated to 168° C., and the reaction water is distilled off together with solvent in the course of 2 hours, the temperature being increased to 180° C. towards the end of the distillation. The pale solids of the suspension are filtered off with suction at 150° C. and dried. The yield of p-sulphanilic acid is 93.8%.

EXAMPLE 26

141 g (1.52 mols) of aniline are initially introduced into a mixture of 350 ml of isododecane and 150 ml of sulpholane, and 147 g (1.50 mols) of 100% strength $H_2SO_4$ are added. The reaction batch is heated for 1.5 hours at 172°–177° C. under a water separator. The solids are filtered off with suction at room temperature and dried. The yield of p-sulphanilic acid is 96.5%.

EXAMPLE 27

94.0 g (1.01 mols) of aniline are initially introduced into a mixture of 400 ml of decaline and 100 ml of sulpholane, and 98.1 g (1.0 mol) of 100% strength $H_2SO_4$ are added dropwise. The temperature is raised to 180° C., and the reaction water is distilled off in the course of 70 minutes. The solids of the suspension are filtered off with suction and dried. The yield of p-sulphanilic acid is 96.2%.

EXAMPLE 28

94.0 g (1.01 mols) of aniline are initially introduced into a mixture of 350 ml of tetralin and 150 ml of sulpholane, and 98.1 g (1.0 mol) of 100% strength $H_2SO_4$ are added. The temperature is increased to 180°–200° C., and the reaction water is distilled off in the course of 50 minutes. The yield of p-sulphanilic acid is 94.5%.

What is claimed is:

1. A process for the preparation of an aminoarylsulphonic acid having a free or neutralized sulphonic acid group which comprises contacting an arylamine of the formula

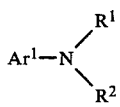

in which
- $R^1$ and $R^2$ independently of one another denote hydrogen, alkyl, aralkyl or aryl, or both together form, together with the N atom on which they are substituted, a nitrogen-containing heterocyclic structure and
- $Ar^1$ represents an unsubstituted or substituted benzene, naphthalene, anthracene naphthoquinone or athraquinone skeleton or the skeleton of an aromatic heterocyclic structure, at a temperature of 120° to 280° C. with a sulphonating agent in a reaction mixture consisting essentially of said arylamine, said sulphonating agent and an inert solvent, said inert solvent comprising tetramethylene sulphone.

2. A process according to claim 1, wherein the reaction mixture contains 10 to 2,000 ml of tetramethylene sulphone per mol of arylamine.

3. A process according to claim 1, wherein the reaction mixture contains in addition to said tetramethylene sulphone, 1 to 99% by volume of another inert solvent.

4. A process according to claim 1, wherein the reaction mixture containing said tetramethylene sulphone is free of another inert solvent.

5. A process according to claim 1, wherein 0.5 to 2.0 mols of sulphonating agent are employed per mol of arylamine.

6. A process according to claim 1, wherein 0.95 to 1.05 mols of sulphonating agent are employed per mol of arylamine.

7. A process according to claim 1, wherein said arylamine is one of the formula

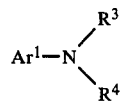

wherein
- $Ar^1$ has the meaning mentioned in claim 1 and
- $R^3$ and $R^4$ independently of one another denote hydrogen or alkyl.

8. A process according to claim 1, wherein said arylamine is one of the formula

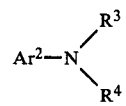

wherein
- $Ar^2$ denotes an optionally substituted benzene or naphthalene skeleton and
- $R^3$ and $R^4$ independently of one another represent hydrogen or alkyl.

9. A process according to claim 1, wherein the sulphonating agent is selected from the group consisting of sulphuric acid, $SO_3$, chlorosulphonic acid and mixtures thereof.

10. A process according to claim 9, wherein the sulphonating agent is sulphuric acid having a water content of 0 to 30% by weight.

11. A process according to claim 1, wherein following the reaction aminoarylsulphonic acid formed is separated from the reaction mixture and the resultant reaction mixture is reused for a further synthesis of aminoarylsulphonic acid without further purification.

12. A process according to claim 1, wherein the process is conducted at a pressure of 0.1 to 100 bar.

13. A process according to claim 1, wherein the process is conducted at a pressure of 1 to 20 bar.

14. A process according to claim 1, wherein the process is conducted in vacuo.

15. A process according to claim 1, wherein the reaction mixture contains 20 to 500 ml of tetramethylene sulphone per mol of arylamine.

16. A process according to claim 1, wherein 0.98 to 1.02 mols of sulphonating agent are employed per mol of arylamine.

17. A process according to claim 1, wherein 1 mol of sulphonating agent is employed per mol of arylamine.

18. A process according to claim 9, wherein the sulphonating agent is sulphuric acid having a water content of 0 to 50%.

19. A process according to claim 9, wherein the sulphonating agent is sulphuric acid having a water content of 0 to 10%.

* * * * *

UNITED STATES PATENT AND TRADEMARK OFFICE
CERTIFICATE OF CORRECTION

PATENT NO. : 4,447,368
DATED : May 8, 1984
INVENTOR(S) : Herbert Emde et al

It is certified that error appears in the above-identified patent and that said Letters Patent is hereby corrected as shown below:

Title page item [54] and Col. 1, line 3,

Delete "SULFOLENE" and substitute --SULFOLANE--

Title page item [73] Assignee: Delete "Siemens-Allis, Inc., Atlanta, Ga." and substitute --BAYER AKTIENGESELLSCHAFT, Leverkusen, Germany--

Signed and Sealed this

Second Day of April 1985

[SEAL]

Attest:

DONALD J. QUIGG

Attesting Officer     Acting Commissioner of Patents and Trademarks